United States Patent [19]

Harrold

[11] Patent Number: 4,590,803
[45] Date of Patent: May 27, 1986

[54] ACOUSTIC WAVEGUIDE MONITORING

[75] Inventor: Ronald T. Harrold, Franklin, Pa.

[73] Assignee: Westinghouse Electric Corp., Pittsburgh, Pa.

[21] Appl. No.: 625,763

[22] Filed: Jun. 28, 1984

[51] Int. Cl.⁴ .......................................... G01N 29/00
[52] U.S. Cl. ................................................... 73/590
[58] Field of Search ................. 73/590, 599, 53, 597

[56] References Cited

U.S. PATENT DOCUMENTS

| | | | |
|---|---|---|---|
| 3,381,525 | 5/1968 | Hartluke et al. | 73/590 |
| 3,654,072 | 4/1972 | Massa | 73/590 |
| 4,054,255 | 10/1977 | Magenheim | 73/170 R |
| 4,312,228 | 1/1982 | Wohltjen | 73/599 |
| 4,327,587 | 5/1982 | Docekal et al. | 73/590 |
| 4,335,613 | 6/1982 | Luukkala | 73/590 |
| 4,524,620 | 6/1985 | Wright et al. | 73/583 |

FOREIGN PATENT DOCUMENTS 2038851 3/1983 United Kingdom .
2027201 5/1983 United Kingdom .

OTHER PUBLICATIONS

Lynnworth, Seventh International Congress on Acoustics, Budapest 1971, "Noninvasive Ultrasonic Measurements for Process Control", pp. 525–528.
Lynnworth et al, IEEE Trans. Nuclear Science, "Nuclear Reactor Applications of New Ultrasonic Transducers", Feb. 1971, pp. 351–362.
Lynnworth et al, IEEE Trans. Nuclear Science, "Ultrasonic Thermometry for Nuclear Reactors", Feb. 1969, pp. 184–187.

Primary Examiner—Anthony V. Ciarlante
Attorney, Agent, or Firm—R. D. Fuerle

[57] ABSTRACT

Disclosed is a method of monitoring physical and chemical changes in a host material which passes from a liquid state to a solid state. A waveguide is embedded in the host material while it is in the liquid or uncured state, the waveguide extending outside of the host material. A sound wave is sent through the waveguide and is monitored after it has passed through the host material. An article is also disclosed of a container having a liquid sealing exit means for waveguide, a waveguide which passes through the liquid sealing exit means into the container, a solidifiable liquid in the container at a level above the liquid sealing exit means, means outside the container for sending an acoustic wave through the waveguide into the container, and means outside the container for monitoring the acoustic wave after it has passed through said waveguide into the container.

20 Claims, 5 Drawing Figures

ACOUSTIC WAVEGUIDE MONITORING

BACKGROUND OF THE INVENTION

When thermosetting resins are cured by a controlled process such as heat, it is often necessary to monitor the degree to which they are cured, so as to know whether to continue the curing process or terminate it. If the resin is undercured, the resulting article will be weak and have poor properties, and if the resin is overcured, time and energy will be wasted and the properties of the resulting article may again begin to deteriorate. One way to monitor the degree of cure is by means of dielectric techniques, where the dielectric constant and dissipation factor of the resin is monitored as it is being cured. However, this method requires that metal electrodes intrude into the resin or contact the resin. Also, due to a poor signal to noise ratio, it is not an ideal procedure for use with graphite-epoxy composites.

The curing process can also be monitored by means of ultrasonic waves. An ultrasonic transmitter is placed on one side of the container and an ultrasonic receiver is placed on the other side and ultrasonic waves are passed through the resin as it cures. While this technique eliminates the intrusion of an electrode into the resin, because of diffusion of the ultrasound beam it is also not extremely sensitive to the physical and chemical changes that are occurring as the resin cures.

SUMMARY OF THE INVENTION

I have discovered that the physical and chemical changes, such as polymerization, that occur when a liquid soldifies can be monitored with extreme sensitivity by passing a sound wave through a waveguide which is embedded in the liquid. This technique is so sensitive that changes in the sound attenuation in the waveguide of 1,000 to 1 or even 10,000 to 1 occur during the curing of the resin.

In addition, once the liquid has solidified, the waveguide remains embedded in the resulting solid and any applied stress or strain can be easily detected by the changes that occur in a sound wave passed through the waveguide. Furthermore, any physical contact with the solid, or structural changes (microcracks) within it, can readily be detected by using the acoustic waveguide as a listening device. For example, a waveguide embedded in a 9 inch by 9 inch graphite-epoxy composite sheet is so sensitive that acoustic waves generated by merely blowing on the sheet or touching it with a feather can easily be detected. As acoustic sensors are bonded to each end of an acoustic waveguide, sonic ranging can be used to locate an acoustic emission site within the cured solid.

RELEVANT ART

U.S. Pat. No. 4,312,228 generates a surface acoustic wave by using an element coated on the surface of a resin being monitored.

U.S. Pat. No. 4,327,587 uses ultrasonic oscillations to monitor polymerization. At least one ultrasonic transducer adapted to both generate and receive ultrasonic waves is used. The transducer is acoustically coupled with an ultrasonic delay line located in the polymerizing monomer.

U.S. Pat. No. 3,654,072 monitors by measuring instantaneous sound transmission using transmitting and receiving transducers located in different regions of a chemical system being monitored.

U.S. Pat. No. 4,335,613 describes waveguide monitoring where a waveguide is placed on the surface of a road in order to detect the formation of ice.

U.S. Pat. No. 4,054,255 is a waveguide to detect ice on aircraft surfaces.

DESCRIPTION OF THE INVENTION

Figure 1:
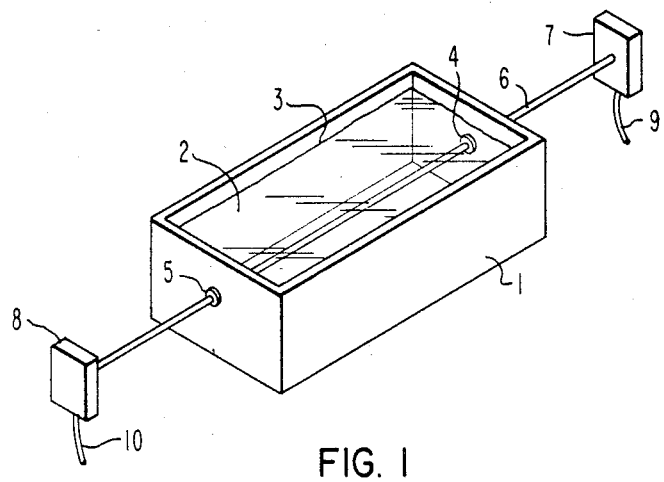
FIG. 1 is an isometric view looking down on a certain presently preferred embodiment of the apparatus according to this invention.

In FIG. 1, a container 1 is filled with a solidifiable liquid 2 up to level 3. The container has liquid seals 4 and 5 in its sides through which passes waveguide 6. To each end of waveguide 6 is affixed a transducer 7 and 8. These transducers convert the electrical energy to sound waves and sound waves back to electrical energy through wires 9 and 10, respectively, which are attached to monitoring equipment (not shown).

Figure 2:
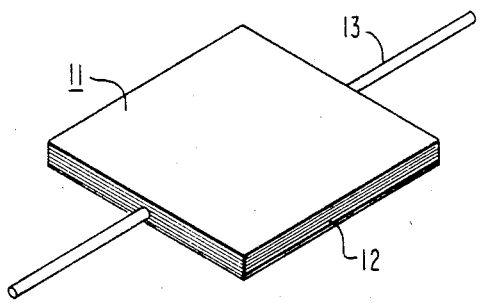
FIG. 2 is an isometric view of a certain presently preferred laminate according to this invention.

In FIG. 2, a laminate 11, consisting of a stack of resin impregnated prepregs 12, has an acoustic waveguide 13 imbedded therein and extending therethrough.

While I do not wish to be bound by any theories, I believe that the amount of sound transmitted through a waveguide is closely related to the difference between the acoustic impedance of the waveguide and the acoustic impedance of, and the pressure exerted by, the host material which surrounds the wavguide, and that the acoustic impedance of the medium which surrounds the waveguide depends upon the density of the host material times the velocity of sound through it. Thus, any physical or chemical changes which affect the density of the host material or the velocity of sound through it will alter its acoustic impedance and change the amount of sound transmitted through the waveguide. Since density and velocity of sound through a host material are affected by temperature, stress, strain, and impact on the host material, all of these things can be monitored by means of the waveguide. It is even possible to calculate Young's modulus from the information obtained through the waveguide. The transit time of the sound wave through the waveguide is also affected by these factors and can also be used to monitor changes that occur in the host material.

The method and apparatus of this invention can be applied to any host material which undergoes a physical change particularly from a liquid to a solid. This includes metals, plastics, cement, and concrete, and the freezing of various liquids. Particularly interesting are prepregs, which are sheets made of a substrate into which a resin has been impregnated and B-staged. The prepregs are stacked with the waveguide in between. Under heat and pressure, the B-staged resin liquefies and cures to bond all the sheets into a laminate.

The waveguide may be made of any material which will not be rendered non-functional by the host material. For example, steel, sapphire, quartz, plastics, glass, polyester-fiberglass, and epoxy-fiberglass can all be used as waveguides. Polyester-fiberglass is the preferred waveguide material for plastic host materials because it is flexible, strengthens the structure of the plastic, and works very well. It is preferable to select a waveguide material which matches the host material in coefficient of thermal expansion to avoid creating stresses in the host material. Also, a good waveguide material will strengthen the resulting article and will bond to the host material. Preferably, the waveguide should have an attenuation of less than about 10 decibels per meter of its length so as to maintain its sensitivity. Of course, if the waveguide is to be very short, higher attenuations would be acceptable. The attenuation depends upon the material out of which the waveguide is constructed as well on its cross-sectional area and the frequency of the sound wave transmitted through the waveguide. Also, attenuation is reduced if the waveguide material and the host material are acoustically mismatched. The waveguide may be of almost any length but longer waveguides, of course, require a more powerful acoustic signal. Although circular waveguides are preferred, the waveguide may be of any cross-sectional shape. The waveguide may be placed anywhere within the host material. If only one waveguide is used, it will generally be placed in the middle of the material. If many waveguides are used, they can be spaced uniformly or they can be placed in more sensitive portions of the host material.

Ultrasonic transducers are used to generate a sound wave in the waveguide. Generally, two transducers will be used, one at each end, one for sending the sound and the other for receiving the sound. The transducers work by changing an electrical signal into a sound signal and, in reverse, by changing a sound signal back into an electrical signal. It is also possible to use a single transducer by bouncing the sound wave off one end of the waveguide so that the sending transducer also becomes the receiving transducer. If a sound wave is bounced off the end of the waveguide, it may be desirable to put an acoustically mismatched material on the end of the waveguide to maximize the reflectance of the sound wave back into the waveguide. To monitor more area within a host material another possible configuration is to bend the waveguide around in a loop so that the sound wave travels from the transducer around through the loop and back to another transducer. It is also possible to transmit the signal through one waveguide and receive it through another after it has passed through the host material.

Any frequency of sound wave that the waveguide will transmit may be used although ultrasonic sound waves, typically about 10 to about 300 kilohertz, are preferred as they give the greatest sensitivity. At lower frequencies, the signal may be obscured by background noise, and at higher frequencies the signal may be attenuated too much. Of course, acoustic filters can be employed to eliminate unwanted noise.

The host material may be cured by various means, including ultraviolet, microwave, electron beam, or other radiation, heat, the addition of catalysts, or even ultrasound. High energy ultrasound for curing purposes can be introduced into the buried waveguides. The resulting structure consists of the solid host material with the waveguide embedded in it. This article is very useful for detecting physical or chemical changes that occur in the host material which affect the attenuation or velocity of sound through it. For example, if the host material is an airplane wing, the waveguide can be used to monitor stress and strain and, by using the waveguide in a listening mode, the velocity of the air passing over the wing or the impact of objects against it can be monitored. The location of the impact of objects against it can be determined by the differences in the time at which the impact is detected at the acoustic sensors bonded to the ends of the waveguide. Alternatively, more than one waveguide can be used to locate the impact site, using the magnitude and time of receipt of the signal.

The following examples further illustrate this invention.

EXAMPLE 1

A 1/16 mm. diameter epoxy-fiberglass acoustic waveguide was inserted through two silicone acoustic isolation seals at each end of two circular polyvinyl chloride containers, each 2¼ inches in diameter, at 1 inch above the bottom of the container. A 74 kHz acoustic transmitter was bonded to one end of the waveguide and a 74 kHz acoustic receiver was bonded to the other end of the waveguide, both outside the container. A bisphenol A epoxy resin sold by Hysol under the trade designation "Epoxi-Patch" was poured into one container to a depth of about 1¼ inches and a gel was poured into a similar container to a similar depth, both about 0.25 inches above the waveguide. The gel consisted of 100 pbw liquid diglycidyl ether of bisphenol A sold by Shell Co. as "Epon 815," 20 pbw amine hardener sold by Texaco "Jeffamine t-403," and 10 pbw of an accelerator sold by Dupont as "Pacm-20." The gel was mixed at 80° C. under vacuum and cured when it was poured into the container. The waveguide for the epoxy was 9⅝ inches long, and the waveguide for the gel was 13¾ inches long. Pulsed acoustic wave trains were transmitted through the waveguides and the received signals were monitored while the resins were poured into the containers and throughout the curing process. As the resins shrunk around the waveguide during the curing process, the signals transmitted through the waveguides were attenuated by about two orders of magnitude. In addition, there were changes in the transit time of the acoustic waves.

Figure 3:
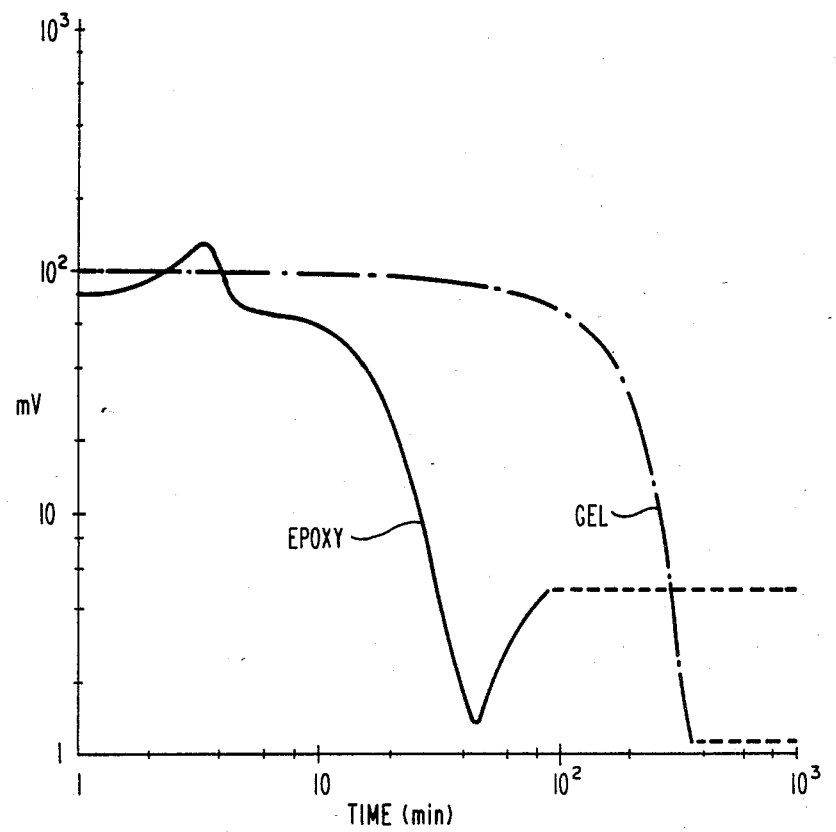
FIGS. 3, 4, and 5 are graphs illustrating the results of experiments described in Examples 1 and 2.

In FIG. 3, the results are given on a graph which plots the peak value of the 74 kHz acoustic signal in millivolts against the time after the resin was poured into the containers. The graph show that, for the epoxy resin, the waveguide transmitted signal was attenuated about 100 to 1 and reached a maximum attenuation after 44 minutes, which is believed to coincide with the end of the curing process. The increase in signal level which occurred later is believed to be due to the resin's return to ambient temperatures, which further indicates the system's sensitivity. The slower curing gel also caused an overall signal attenuation of about 100 to 1 but the maximum attenuation was not reached until after 350 minutes.

Figure 4:
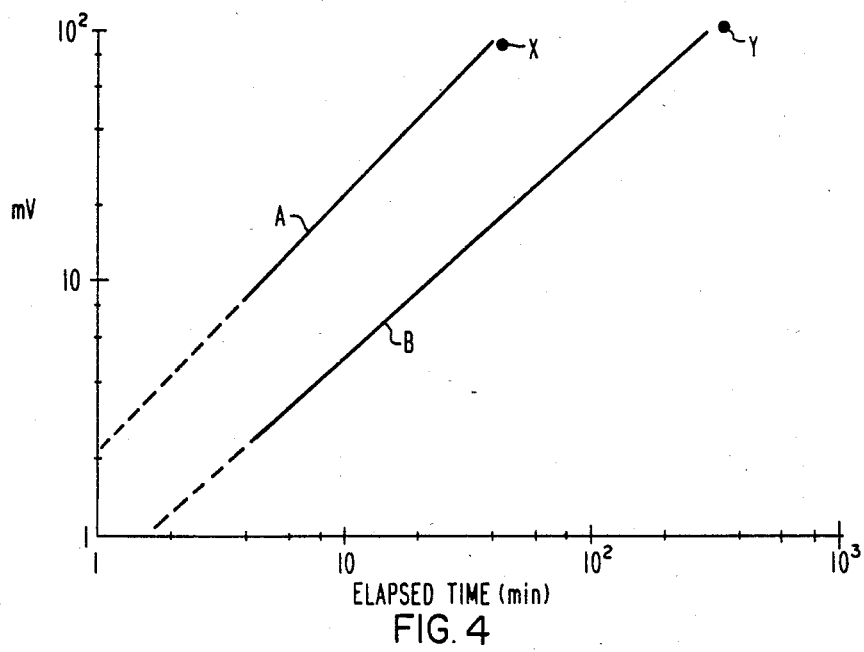

FIG. 4 is a graph which plots, in millivolts, the difference between the initial acoustic signal and the signal at the time given on the horizontal axis. Curve A is for the epoxy resin and curve B is for the gel. Curve A fits the equation $V_0 - V = 2.1\, t^{1.03}$ and curve B fits the equation $V_0 - V = 0.66\, t^{0.88}$. Point X is the completion of cure for the epoxy resin and point Y is the completion of cure for the gel. The straight lines produced by the data indicate that the polymerization and gellation processes are following first order chemical reactions and that the attenuation of the acoustic wave corresponds to the polymerization of the resin. From these equations it is possible to predict early in the curing process the approximate time needed for completion of the process.

EXAMPLE 2

Thirty six 6 inch by 6 inch prepregs of 9 micron graphite fiber impregnated with an epoxy resin, sold by Hercules under the trade designation "3501-6/AS" were stacked in alternative directions, except for the middle two prepregs, which were parallel. A 36 inch polyester-fiberglass acoustic waveguide 1/16 inch thick was placed between the middle two prepregs, parallel to the fibers.

The ends of the waveguide were bonded to 70 kHz ultrasonic transducers. The transducers were electrically connected to preamplifiers and filters, then to an oscilloscope.

Figure 5:
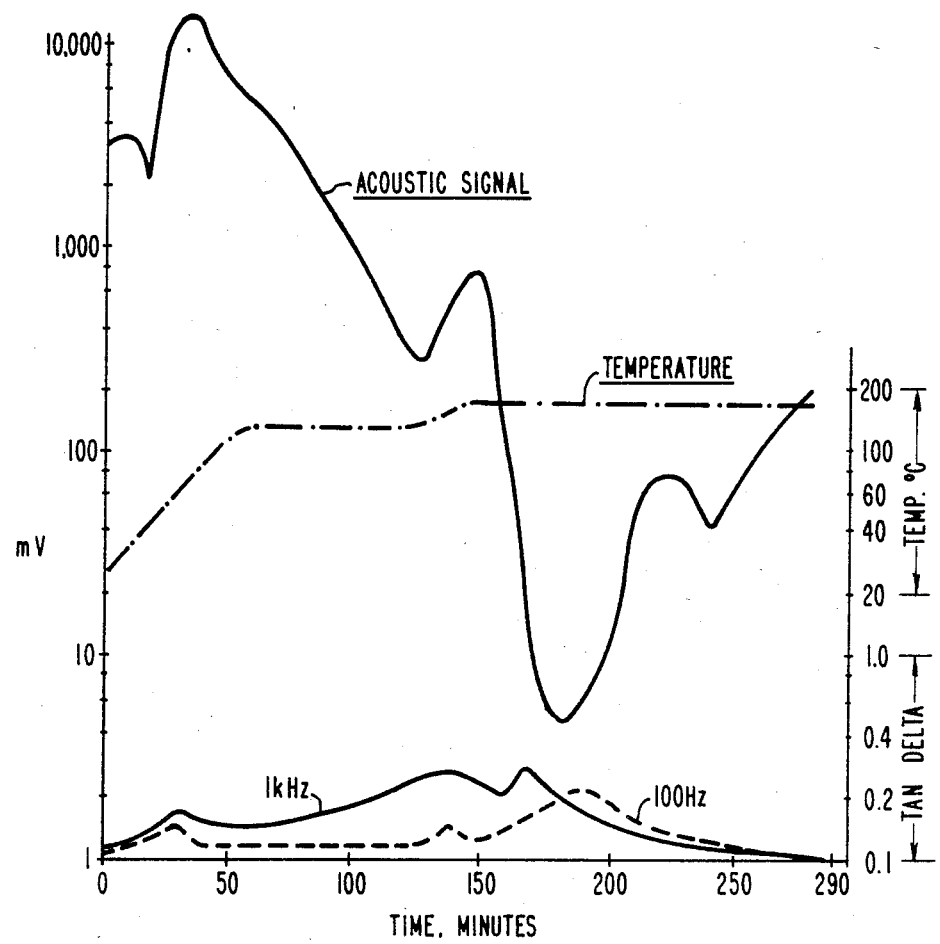

A laminate was made by pressing the stack of prepregs at 50 lbs/inch$^2$ while heating to cure the resin. FIG. 5 gives the temperature of the stack versus time. Also on FIG. 5 is the peak acoustic signal received at 71 kHz during cure. A signal of about 3000 microvolts was sent through the waveguide by means of one of the transducers during cure.

At the bottom of FIG. 5 is given the results of using automatic dielectrometry at 1 kHz and 100 Hz to monitor the cure of an identical stack of prepregs over the same timer period.

The results given in FIG. 5 show that the method of this invention is many times more sensitive than automatic dielectrometry, which is presently the established method of monitoring cure.

EXAMPLE 3

Example 2 was repeated using identical materials and procedures except that the prepregs were 9 inches by 9 inches and the waveguide was epoxy-fiberglass. The sensitivity of the waveguide was tested by dropping single grains of salt onto the laminate from a height of 25 cm. The impact of each grain generated an acoustic signal of about 1000 microvolts in the waveguide, making each impact easily detectable. Even very lightly touching the laminate with a feather generated a noticeable signal in the waveguide.

I claim:

1. A method of monitoring physical or chemical changes in a resinous host material that passes from a liquid state to a solid state comprising:
   (1) placing a waveguide in said resinous host material while it is in said liquid state, said waveguide extending outside of said resinous host material;
   (2) solidifying said host material, embedding said waveguide therein; and
   (3) monitoring sound waves in said waveguide after said sound waves have passed through said waveguide in said material.

2. A method according to claim 1 including the additional step between steps (1) and (2) of transmitting a sound wave through said waveguide.

3. A method according to claim 2 wherein said host material comprises a thermosettable plastic.

4. A method according to claim 2 wherein said waveguide comprises fiberglass.

5. A method according to claim 2 wherein said sound has a wavelength of about 10 to about 300 kilohertz.

6. A method according to claim 2 wherein said host material is an airplane wing.

7. A method according to claim 1 wherein stress is monitored in said host material after it has solidified.

8. A method according to claim 1 wherein the temperature of said host material is monitored using said sound waves.

9. A method of monitoring the curing of a thermosettable resin in a liquid form comprising placing a waveguide in said resin extending outside of said resin, and curing said resin while monitoring acoustic waves sent through said waveguide.

10. A method according to claim 9 wherein said thermosettable resin is a B-staged resin in prepregs, said waveguide is placed between prepregs, and said resin in said prepregs liquifies during preparation of said laminate.

11. Apparatus comprising:
   (A) a container;
   (B) an acoustic waveguide passing into in said container from a point outside said container passing through said container below the top of said container, to a second point outside said container;
   (C) a solidifiable resinous liquid in said container to a level above said waveguide;
   (D) means outside said container attached to one end of said waveguide for sending an acoustic wave through said waveguide into said container; and
   (E) means outside said container attached to the other end of said waveguide for monitoring said acoustic wave after it has passed through said waveguide in said container.

12. Apparatus according to claim 11 wherein said solidifiable liquid is a B-staged resin on a prepreg which is liquefied under heat and pressure.

13. Apparatus according to claim 11 including entrance and exit apertures in said container through which said waveguide passes.

14. An article comprising:
   (A) a laminate which comprises a resin impregnated substrate having an acoustic waveguide embedded therein and extending therefrom; and
   (B) means attached to said acoustic waveguide for monitoring sound waves that travel along it.

15. An article according to claim 14 including means for generating an acoustic signal in said waveguide.

16. An article according to claim 14 in the shape of an airplane wing.

17. An article according to claim 14 wherein said waveguide has an attenuation of less than about 10 decibels per meter of its length.

18. A method of monitoring physical changes in an airplane wing having a composite structure made of a stack of prepregs bonded together comprising:
   (1) placing a waveguide inbetween said prepregs in said stack before they are bonded together, with at least one end of said waveguide extending outside of said stack of prepregs;
   (2) bonding said stack of prepregs into a laminate;
   (3) attaching a transducer to said end of said waveguide to convert sound waves that travel along said waveguide into an electrical signal; and
   (4) using said electrical signal to monitor said sound waves.

19. A method of monitoring physical or chemical changes in a liquid resinous host material comprising:
   (1) placing a waveguide in said liquid resinous host material with both ends of said waveguide extending outside of said host material;
   (2) transmitting a sound wave along said waveguide from one end of said waveguide;
   (3) receiving and monitoring said sound wave at the other end of said waveguide.

20. A method according to claim 19 wherein said liquid resinous host material solidifies around said waveguide, permanently embedding it therein.

* * * * *